(12) United States Patent
Sampson

(10) Patent No.: US 9,089,384 B1
(45) Date of Patent: Jul. 28, 2015

(54) DENTAL PIN SYSTEM

(71) Applicant: Austin H. Sampson, Clearwater, FL (US)

(72) Inventor: Austin H. Sampson, Clearwater, FL (US)

( * ) Notice: Subject to any disclaimer, the term of this patent is extended or adjusted under 35 U.S.C. 154(b) by 0 days.

(21) Appl. No.: 14/280,622

(22) Filed: May 18, 2014

Related U.S. Application Data

(60) Provisional application No. 61/825,927, filed on May 21, 2013.

(51) Int. Cl.
| | |
|---|---|
| *A61C 5/04* | (2006.01) |
| *A61C 3/02* | (2006.01) |
| *A61C 13/38* | (2006.01) |
| *A61C 1/08* | (2006.01) |
| *A61C 5/00* | (2006.01) |

(52) U.S. Cl.
CPC .. *A61C 1/08* (2013.01); *A61C 5/005* (2013.01)

(58) Field of Classification Search
CPC ............ A61C 1/14; A61C 1/145; A61C 3/00; A61C 5/005; A61C 8/0028; A61C 8/0022; A61C 8/0089; A61C 1/08
USPC ........... 433/172–176, 165, 225, 77; 82/124.2, 82/124.4, 121.1, 177.2, 177.1; 206/368–369; 81/124.2, 124.4, 121.1, 81/177.2, 177.1
See application file for complete search history.

(56) References Cited

U.S. PATENT DOCUMENTS

| | | |
|---|---|---|
| 2,289,785 A | 7/1942 | Hutchison, Jr. |
| 2,310,409 A | 2/1943 | Ellman |

(Continued)

FOREIGN PATENT DOCUMENTS

| | | |
|---|---|---|
| EP | 0260446 B1 | 3/1992 |
| EP | 0570081 A2 | 11/1993 |

(Continued)

OTHER PUBLICATIONS

TMS Link / TMS Link Plus Product Details, Coltene Whaledent Website, Web page <http://www.coltene.com/en/products/17/details/36/TMS_LINK_-_TMS_LINK_PLUS.html>, 4 pages, dated Aug. 24, 2010, retrieved from Internet Archive Wayback Machine <https://web.archive.org/web/20100824192849/http://www.coltene.com/en/products/17/details/36/TMS_LINK_-_TMS_LINK_PLUS.html> on Jul. 12, 2014.

(Continued)

*Primary Examiner* — Heidi M Eide
(74) *Attorney, Agent, or Firm* — The Law Office of Patrick F. O'Reilly III, LLC

(57) ABSTRACT

A dental pin system is disclosed herein. The dental pin system includes one or more dental pins and a chuck member for inserting the one or more dental pins into one or more teeth of a patient. The one or more dental pins each include a body portion having a threaded surface, a cap portion coupled to the body portion, and a projection extending from an upper surface of the cap portion. The chuck member includes a body portion having a first end section and a second end section, a recess formed in the first end section of the body portion, and a groove formed in the first end section which intersects the recess. The second end section of the body portion of the chuck member is configured to be removably coupled to a dental tool that drives the chuck member. The dental pin system may also include a dispenser.

19 Claims, 10 Drawing Sheets

Detail "A"

(56) References Cited

U.S. PATENT DOCUMENTS

| | | | |
|---|---|---|---|
| 3,364,575 A | 1/1968 | Baker | |
| 3,434,209 A | 3/1969 | Weissman | |
| 3,576,073 A | 4/1971 | Weissman | |
| 3,629,943 A | 12/1971 | Gindea | |
| 3,646,677 A | 3/1972 | Saupe et al. | |
| 3,675,328 A * | 7/1972 | Weissman | 433/225 |
| 3,675,329 A | 7/1972 | Weissman | |
| 3,861,043 A * | 1/1975 | Lieb et al. | 433/225 |
| 3,875,665 A | 4/1975 | Weissman | |
| 3,932,939 A | 1/1976 | Weissman | |
| RE29,817 E | 10/1978 | Lieb et al. | |
| 4,187,611 A | 2/1980 | Chan | |
| 4,189,834 A | 2/1980 | Smith | |
| 4,202,101 A | 5/1980 | Weissman | |
| 4,349,335 A | 9/1982 | Weissman | |
| 4,365,958 A * | 12/1982 | Vlock | 433/225 |
| 4,371,342 A | 2/1983 | Filhol | |
| 4,397,395 A * | 8/1983 | McKelvey | 211/69 |
| 4,451,237 A | 5/1984 | Filhol | |
| 4,655,711 A * | 4/1987 | Weissman | 433/225 |
| 4,684,555 A | 8/1987 | Neumeyer | |
| 4,692,116 A | 9/1987 | Filhol | |
| 4,850,874 A | 7/1989 | Weissman | |
| 4,917,606 A | 4/1990 | Miller | |
| D314,821 S | 2/1991 | Miller | |
| D314,822 S | 2/1991 | Miller | |
| 5,035,620 A | 7/1991 | Roane | |
| 5,051,092 A | 9/1991 | Miller | |
| D321,560 S | 11/1991 | Miller | |
| 5,073,112 A | 12/1991 | Weil | |
| 5,087,201 A * | 2/1992 | Mondani et al. | 433/174 |
| D324,731 S | 3/1992 | Sullivan | |
| 5,094,618 A | 3/1992 | Sullivan | |
| 5,104,321 A | 4/1992 | Filhol | |
| 5,263,996 A | 11/1993 | Filhol | |
| D342,314 S | 12/1993 | Miller | |
| D358,212 S | 5/1995 | Sullivan | |
| D366,115 S | 1/1996 | Sullivan | |
| 5,482,465 A | 1/1996 | Filhol | |
| 5,568,757 A * | 10/1996 | Lewis | 81/177.2 |
| 5,743,734 A * | 4/1998 | Heath et al. | 433/77 |
| 6,536,977 B1 * | 3/2003 | Hammel | 401/205 |
| D567,378 S | 4/2008 | Nordahl et al. | |
| 7,611,355 B2 * | 11/2009 | Murias | 433/174 |
| 7,677,891 B2 * | 3/2010 | Niznick | 433/174 |
| 7,878,093 B1 * | 2/2011 | Peterman | 81/124.2 |
| 7,967,605 B2 | 6/2011 | Goodis | |
| 8,227,018 B2 | 7/2012 | Mannschedel et al. | |
| 2005/0103663 A1 * | 5/2005 | Jolley et al. | 206/366 |
| 2006/0160047 A1 * | 7/2006 | Ellison | 433/174 |
| 2006/0188842 A1 | 8/2006 | Mannschedel et al. | |
| 2009/0220909 A1 | 9/2009 | Muller et al. | |
| 2013/0071814 A1 | 3/2013 | Boehner et al. | |
| 2014/0175114 A1 * | 6/2014 | Southgate | 221/185 |

FOREIGN PATENT DOCUMENTS

| | | |
|---|---|---|
| EP | 0387334 B1 | 6/1994 |
| EP | 0400102 B1 | 8/1995 |
| EP | 1371343 A1 | 12/2003 |
| EP | 2090280 A1 | 8/2009 |
| EP | 2172169 A1 | 4/2010 |
| FR | 1202335 A | 1/1960 |
| GB | 1580356 A | 12/1980 |
| WO | 8805289 A1 | 7/1988 |
| WO | 0025698 A1 | 5/2000 |

OTHER PUBLICATIONS

TMS Link Series Instructions, Web page <http://www.coltene.com/download.php?file_id=4153>, 2 pages, dated Aug. 24, 2010 or before, retrieved from Internet Archive Wayback Machine <https://web.archive.org/web/20140713000838/http://www.coltene.com/download.php?file_id=4153> on Jul. 12, 2014.

Filpin and Filpost Products, Filhol Website, Web page <http://filhol.com/>, 1 page, dated Feb. 3, 2011, retrieved from Internet Archive Wayback Machine <https://web.archive.org/web/20110203024300/http://filhol.com/> on Jul. 12, 2014.

"TMS Link and TMS Link Plus: Its the details that make the difference", 1 page, dated Mar. 13, 2013 or before, retrieved from Coltene Whaledent Website <http://www.coltene.com> on Mar. 13, 2013.

TMS Thread Mate System—Regular Manual Placement Kits, 1 page, dated Jul. 12, 2014 or before, retrieved from Patterson Dental Website <http://www.pattersondental.com> on Jul. 12, 2014.

TMS Thread Mate System—Self-Shearing Minikin Manual Placement Kits, 1 page, dated Jul. 12, 2014 or before, retrieved from Patterson Dental Website <http://www.pattersondental.com> on Jul. 12, 2014.

* cited by examiner

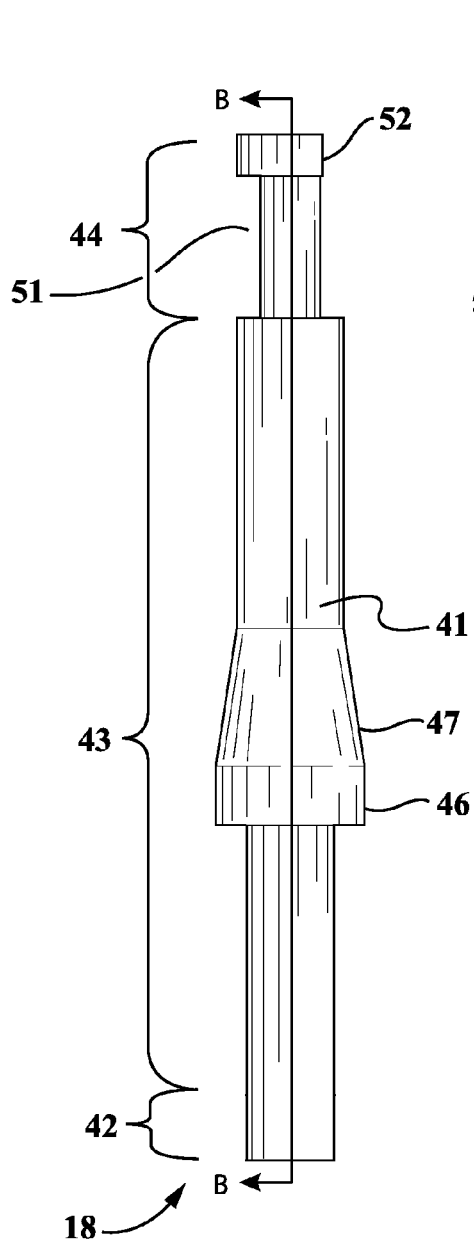
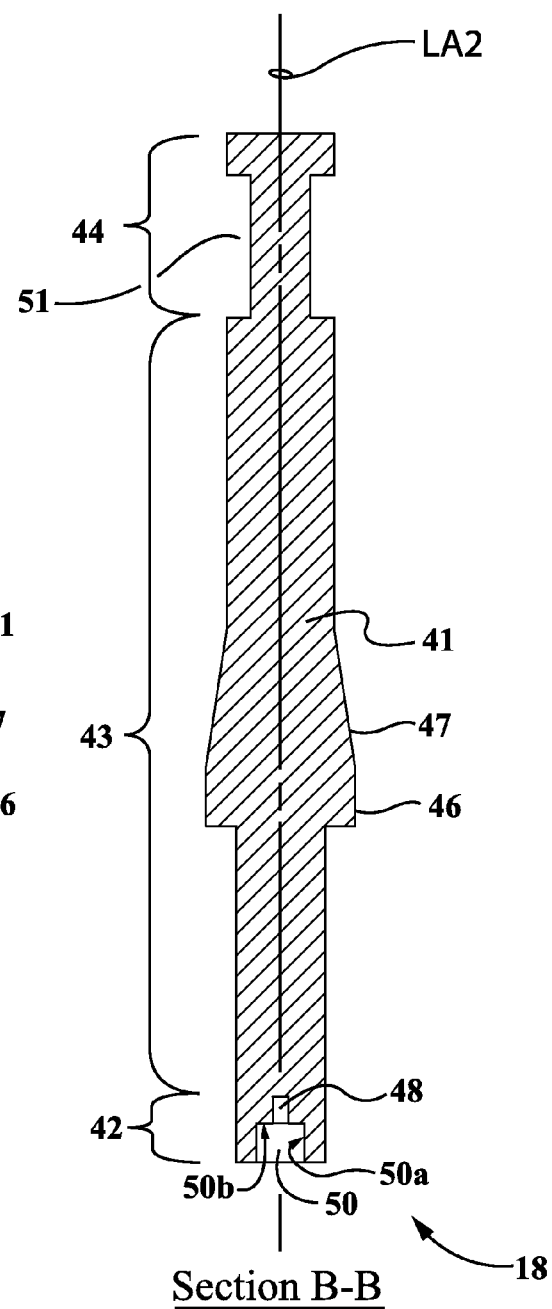
FIG. 7
Section B-B
FIG. 8

Section C-C

Detail "A"

Detail "B"

Section A-A

US 9,089,384 B1

DENTAL PIN SYSTEM

CROSS-REFERENCE TO RELATED APPLICATIONS

This patent application claims priority to, and incorporates by reference in its entirety, U.S. Provisional Patent Application No. 61/825,927, entitled "DENTAL PIN SYSTEM", filed on May 21, 2013.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a dental pin system. More particularly, the invention pertains to a dental pin system that is utilized in restorative dental procedures performed on teeth.

2. Background

In the dental operation of using a mechanical attachment mechanism to secure a reinforcing foundation to a decayed or broken tooth, anchoring pins are driven into the tooth structure. These anchoring pins retain a superstructure that serves as a foundation for a crown restoration. Most of the systems currently available utilize a self-shearing or separating mechanism to insert the pin. The anchoring pin is driven into the tooth while the driver, or chuck, separates and is retained by the dental handpiece or contra-angle. Once the shearing process has occurred, the anchoring pin is left without a cap.

It has been demonstrated by scientific studies that the separation procedure causes vibration that has been shown to cause structural damage to the internal tissue of the tooth, referred to as dentin. This type of insertion technique also frequently weakens the retention of the anchoring pin, due to either premature separation or failure to separate. In addition, premature separation poses the risk of operator loss of control and potential trauma to neighboring structures.

This insertion technique has been shown to cause damage in both healthy and unhealthy dentin, although the damage to unhealthy dentin is far more severe. Further shortcomings of the current systems are that the materials used and the unreliability of the separation process can restrict the operator from employing the necessary force to completely drive the pin into place, thereby lessening retention.

Because the current systems require that the operator manually pick up and load the pin mechanism into the driver, there is a lack of control over the aspect of cross-contamination with surgical gloves and pins.

Therefore, what is needed is a dental pin system that utilizes a separate, reusable chuck for effectively driving the dental pin into the tooth. Moreover, a dental pin system is needed that includes a dental pin that, once it has separated from its chuck, has a cap that provides more torque to drive it and provides increased retention of the core material on the tooth being repaired. Furthermore, there is a need for a dental pin system, which includes an effective and hygienic means by which to dispense and insert the pins into one or more teeth.

BRIEF SUMMARY OF EMBODIMENTS OF THE INVENTION

Accordingly, the present invention is directed to a dental pin system that substantially obviates one or more problems resulting from the limitations and deficiencies of the related art.

In accordance with one or more embodiments of the present invention, there is provided a dental pin for insertion into a tooth, the dental pin including a body portion having a first end, a second end disposed opposite to the first end, and a first diameter, the body portion further including a threaded surface; a cap portion having a first end, a second end disposed opposite to the first end, and a second diameter, the first end of the cap portion coupled to the second end of the body portion, the second diameter of the cap portion being greater than the first diameter of the body portion so as to form an overhanging lip at the location where the first end of the cap portion is coupled to the second end of the body portion; and a projection extending from an upper surface of the cap portion, the projection configured to matingly engage with a corresponding groove in a chuck member.

In a further embodiment of the present invention, the threaded surface of the body portion of the dental pin comprises a plurality of buttress threads, each of the plurality of buttress threads having an upper surface and a lower surface.

In yet a further embodiment, the upper and lower surfaces of the plurality of buttress threads form cross-sectional angles of between approximately 40.5 degrees and approximately 49.5 degrees.

In still a further embodiment, the upper and lower surfaces of the plurality of buttress threads form cross-sectional angles of approximately 45 degrees.

In yet a further embodiment, the body portion of the dental pin further comprises a central longitudinal axis, the upper surfaces of the plurality of buttress threads being disposed generally perpendicular to the central longitudinal axis, and the lower surfaces of the plurality of buttress threads being disposed at an acute angle relative to the central longitudinal axis.

In still a further embodiment, the threaded surface of the body portion comprises a plurality of coarse threads.

In yet a further embodiment, the threaded surface of the body portion comprises a plurality of fine threads.

In still a further embodiment, the first end of the body portion comprises a pointed tip.

In yet a further embodiment, the pointed tip of the body portion of the dental pin comprises a plurality of recessed facets.

In still a further embodiment, the body portion of the dental pin comprises a non-threaded surface between the pointed tip and the threaded surface so as to facilitate heat dissipation.

In yet a further embodiment, each of the body portion and the cap portion of the dental pin is generally cylindrical in shape.

In still a further embodiment, the projection of the dental pin has a generally rectilinear shape.

In yet a further embodiment, the projection of the dental pin extends a predetermined distance above the upper surface of the cap portion.

In still a further embodiment, the dental pin comprises gold-plated stainless steel.

In yet a further embodiment, the dental pin has an overall length between approximately 4.0 millimeters and approximately 4.9 millimeters.

In accordance with one or more other embodiments of the present invention, there is provided a chuck member for inserting a dental pin into a tooth, the chuck member including a body portion having a first end section, a second end section disposed opposite to the first end section, and a middle section disposed between the first and second end sections, the second end section of the body portion configured to be removably coupled to a dental tool that drives the chuck member; a recess formed in the first end section of the body portion, the recess being bounded by one or more side surfaces and an end surface, the recess configured to be removably coupled to a cap portion of a dental pin; and a groove formed in the first end section of the body portion and intersecting the recess, the groove bisecting the end surface of the recess, the groove configured to be removably coupled to a projection of a dental pin.

In a further embodiment of the present invention, the second end section of the body portion of the chuck member comprises a semi-circular groove formed therein, the semi-circular groove configured to matingly engage with one or more components of the dental tool.

In yet a further embodiment, the second end section of the body portion of the chuck member further comprises a radial flat formed on one side thereof, the radial flat configured to interlock the chuck member with a rotating component of the dental tool.

In still a further embodiment, the middle section of the body portion of the chuck member includes an outwardly extending skirt for stabilizing the chuck member as it is being driven by the dental tool.

In yet a further embodiment, at least a portion of the outwardly extending skirt of the chuck member has a generally frusto-conical shape.

In still a further embodiment, the recess formed in the first end section of the body portion of the chuck member is generally cylindrical in shape.

In yet a further embodiment, the groove formed in the first end section of the body portion of the chuck member has a generally rectilinear shape.

In still a further embodiment, the chuck member is formed from stainless steel.

In accordance with yet one or more other embodiments of the present invention, there is provided a dental pin system that includes: (i) a chuck member for inserting a dental pin into a tooth, the chuck member comprising a chuck body portion having a first end section, a second end section disposed opposite to the first end section, and a middle section disposed between the first and second end sections, the second end section of the chuck body portion configured to be removably coupled to a dental tool that drives the chuck member; a recess formed in the first end section of the chuck body portion, the recess being bounded by one or more side surfaces and an end surface; and a groove formed in the first end section of the chuck body portion and intersecting the recess, the groove bisecting the end surface of the recess; and (ii) a dental pin comprising a pin body portion having a first end, a second end disposed opposite to the first end, and a first diameter, the pin body portion further including a threaded surface; a pin cap portion having a first end, a second end disposed opposite to the first end, and a second diameter, the first end of the pin cap portion coupled to the second end of the pin body portion, the second diameter of the pin cap portion being greater than the first diameter of the pin body portion so as to form an overhanging lip at the location where the first end of the pin cap portion is coupled to the second end of the pin body portion, the pin cap portion configured to be removably coupled to the recess of the chuck member; and a projection extending from an upper surface of the pin cap portion, the projection configured to be removably coupled to the groove of the chuck member.

In a further embodiment of the present invention, the dental pin system further comprises a dispenser for removably supporting one or more of the dental pins prior to the dental pins being inserted into a tooth, the dispenser having an upper surface, one or more side surfaces, and a lower surface, the upper surface of the dispenser including one or more recesses disposed therein for removably receiving the one or more dental pins, wherein at least a portion of the pin body portion of each of the one or more dental pins is disposed within its respective the recess, and the pin cap portion of each of the one or more dental pins is exposed above the upper surface of the dispenser such that the pin cap portion is capable of being removably coupled to the recess of the chuck member.

In yet a further embodiment, the lower surface of the dispenser has a central recess formed therein, and wherein the lower surface of the dispenser is in the form of a peripheral surface that circumscribes the central recess.

In still a further embodiment, the one or more recesses in the upper surface of the dispenser are generally cylindrical in shape.

In yet a further embodiment, the one or more recesses in the upper surface of the dispenser comprise first and second pluralities of recesses, the first and second pluralities of recesses being separated from one another by a non-perforated portion of the upper surface of the dispenser.

In still a further embodiment, the first plurality of recesses comprises a first indicia disposed proximate thereto, and the second plurality of recesses comprises a second indicia disposed proximate thereto.

In yet a further embodiment, the first indicia comprises one or more letters or markings that indicate to a user that the first plurality of recesses comprise the one or more dental pins with fine threads, and wherein the second indicia comprises one or more letters or markings that indicate to the user that the second plurality of recesses comprise the one or more dental pins with coarse threads.

In still a further embodiment, the lower surface of the dispenser comprises a skid-resistant layer disposed thereon that is adapted to minimize the movement of the dispenser during use.

In yet a further embodiment, at least one of the one or more side surfaces comprises an indentation to enhance a grip of a user.

In still a further embodiment, at least one of the one or more side surfaces additionally comprises scoring, knurling, and/or spaced apart projections to further enhance a grip of a user.

In yet a further embodiment, the dispenser has a generally cubical shape.

In still a further embodiment, the dispenser is formed of an elastomeric material.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 7 is a side elevational view of the chuck of FIG. 6;

FIG. 8 is a longitudinal sectional view of the chuck of FIG. 6, which is cut along the cutting-plane line B-B in FIG. 7;

Throughout the figures, the same parts are always denoted using the same reference characters so that, as a general rule, they will only be described once.

DETAILED DESCRIPTION OF EMBODIMENTS OF THE INVENTION

Figure 1:
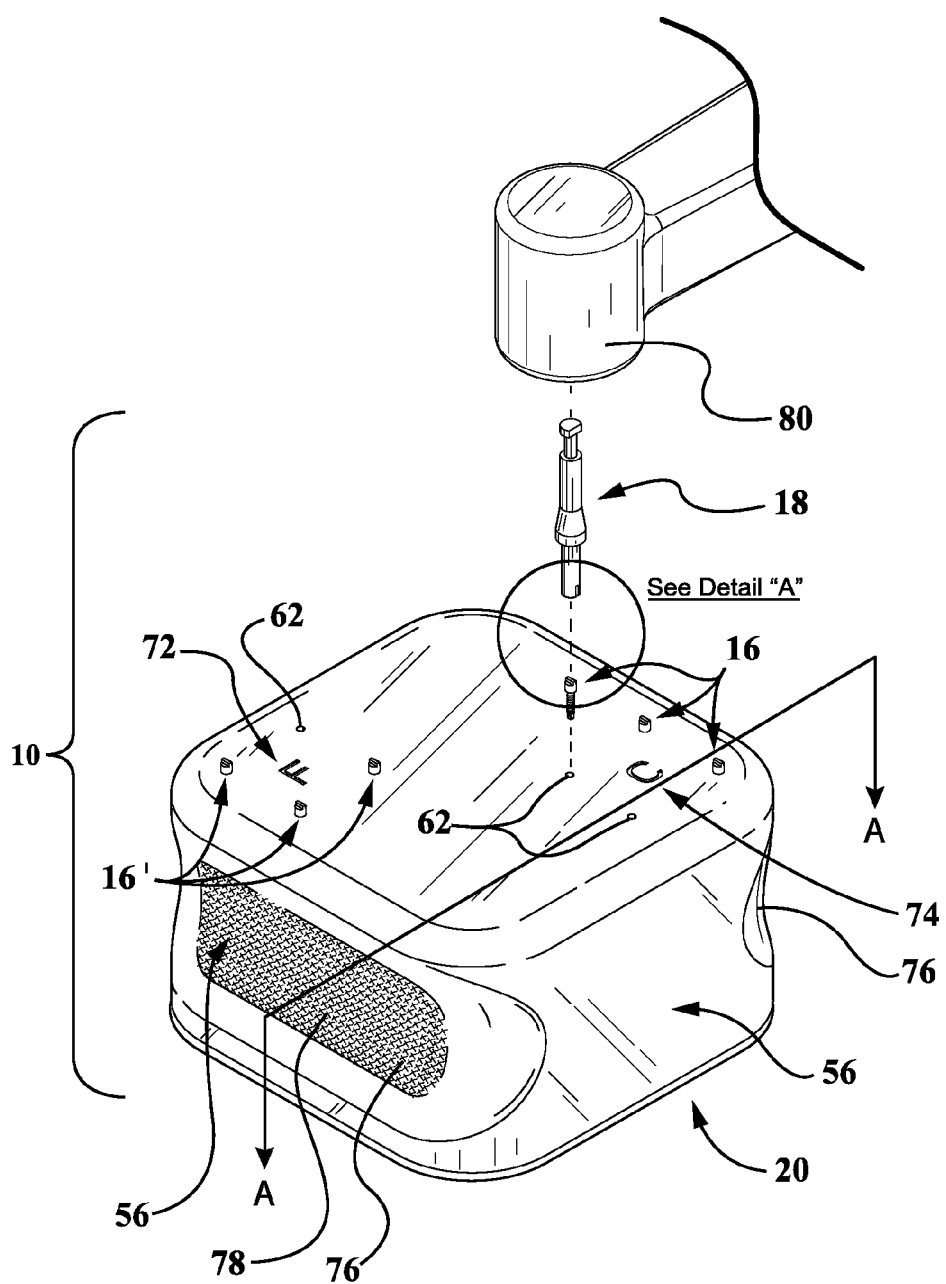
FIG. 1 is a perspective view of a dental pin system, according to an embodiment of the invention, wherein the dental pin system is illustrated in conjunction with a dental tool.

With reference now to the drawings, and in particular to FIG. 1 thereof, the illustrative embodiments of the new and improved dental pin system embodying the principles and concepts of the present invention and generally designated by the reference numeral 10 will be described.

In one or more illustrative embodiments, the dental pin system 10 is comprised of a plurality of components. Such components are individually configured and correlated with respect to each other so as to attain the desired objective. In the broadest context, first provided is a pin in a generally cylindrical configuration with a central axis. The pin has a distal end, a proximal end, and a threaded surface between the distal and proximal ends. The threaded surface is formed with buttress threads having generally horizontal upper surfaces perpendicular to the central axis. The buttress threads have angled lower surfaces. The upper and lower surfaces may form cross sectional angles of between about 43.5 and about 46.5 degrees, inclusive (or between 43.5 and 46.5 degrees, inclusive). The distal end is formed with facets for self-tapping purposes. Such components are individually configured and correlated with respect to each other so as to attain the desired objective.

The illustrative embodiment of the system, designated by reference numeral 10 in the drawings, is to serve as a support for core foundations when inserted into both healthy and sclerotic dentin. The system utilizes a pin 16, a chuck 18 for inserting the pin into the tooth, and a dispenser 20 for removably supporting the pin prior to inserting. The supporting and inserting and restoring are done in a hygienic, safe, rapid, convenient and economical manner.

Figure 18:
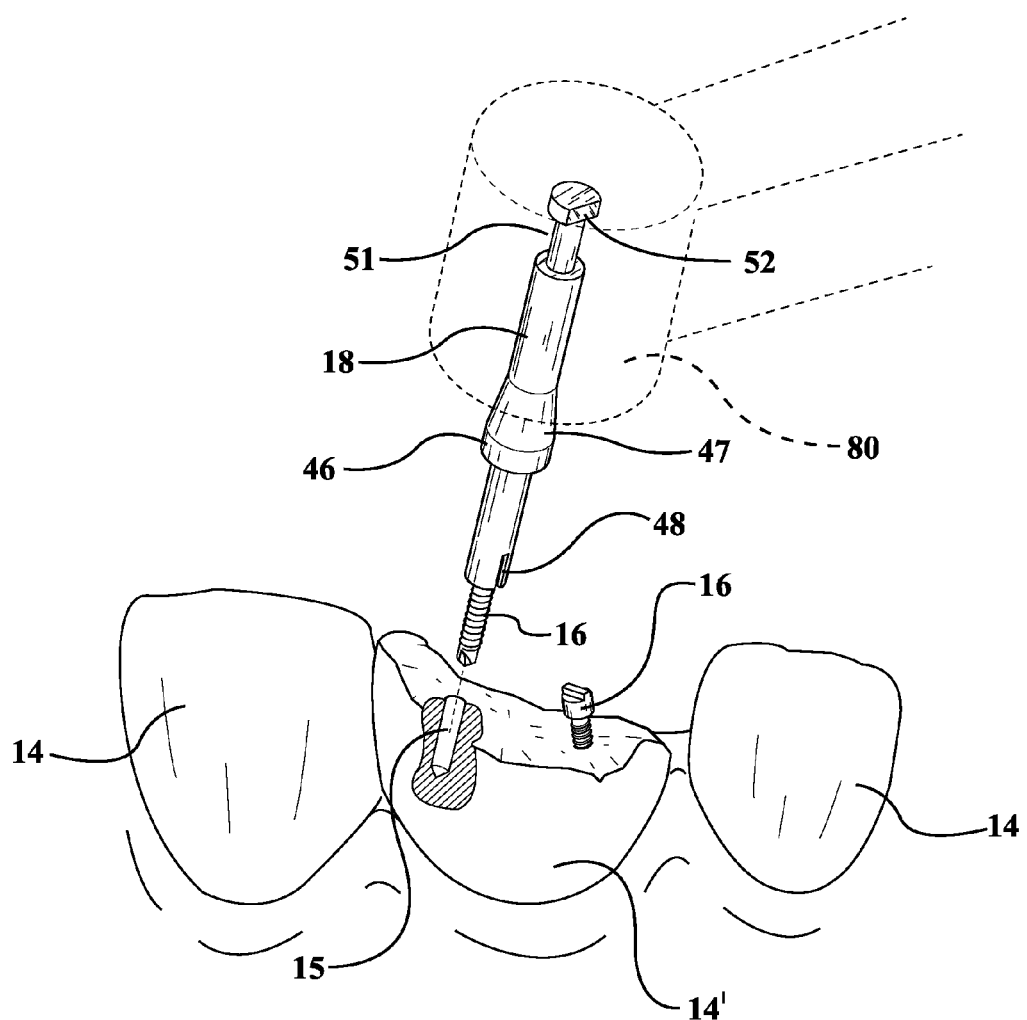
FIG. 18 is a perspective view illustrating the manner in which the dental pins of the dental pin system of FIG. 1 are inserted into a sclerotic tooth of a patient.

Referring to FIG. 18, a brittle, high sclerotic tooth 14' of an aged patient has a tooth structure exteriorly and a tooth core interiorly. The tooth structure and the tooth core are to be reinforced for increased strength. The tooth has an exposed exterior surface.

Figure 2:
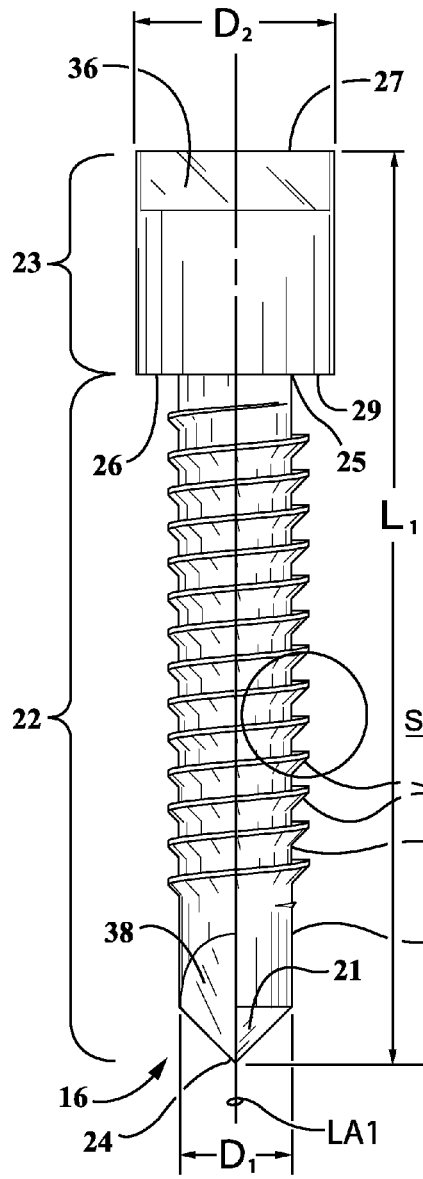
FIG. 2 is a side elevational view of a dental pin of the dental pin system of FIG. 1.
Figure 3:
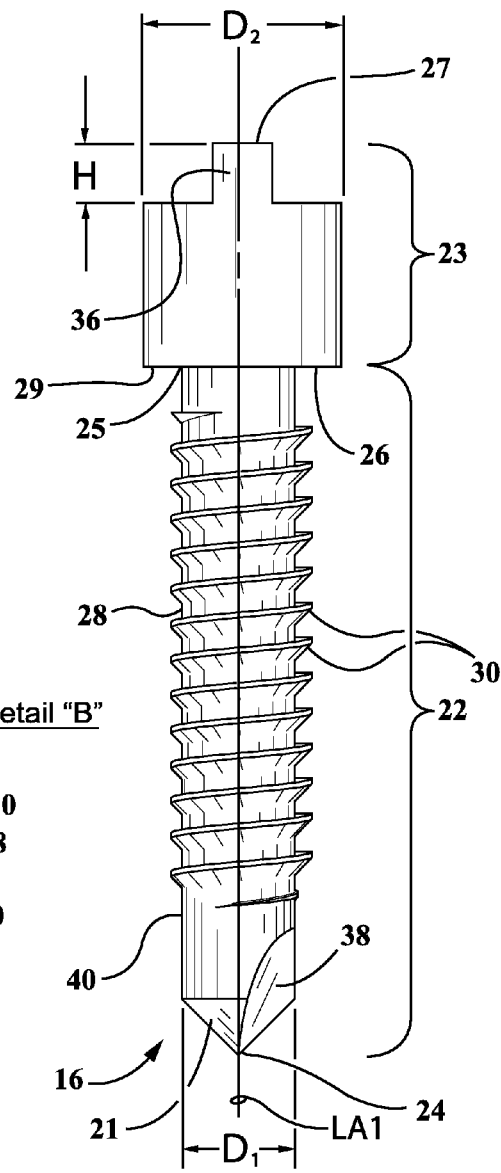
FIG. 3 is a front elevational view of the dental pin of FIG. 2.
Figure 4:
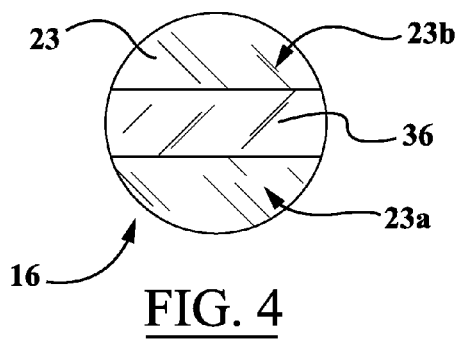
FIG. 4 is a top plan view of the dental pin of FIG. 2.
Figure 5:
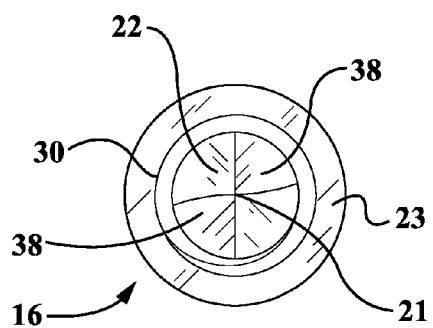
FIG. 5 is a bottom plan view of the dental pin of FIG. 2.

With reference to FIGS. 2-5, a pin 16 of the exemplary dental pin system 10 will be explained in detail. Initially, referring to FIGS. 2 and 3, it can be seen that the dental pin 16 has a generally cylindrical configuration with a central longitudinal axis LA1 disposed axially through the center thereof. The dental pin 16 generally includes a body portion 22 and a cap portion 23 disposed above the body portion 22. As shown in FIGS. 2 and 3, the body portion 22 of the dental pin 16 has a first end 24, a second end 25 disposed opposite to the first end 24, and a first diameter $D_1$. The body portion 22 of the dental pin 16 includes a threaded surface 28 disposed along the length thereof. Referring again to FIGS. 2 and 3, it can be seen that the generally cylindrical cap portion 23 of the dental pin 16 has a first end 26, a second end 27 disposed opposite to the first end 26, and a second diameter $D_2$. The first end 26 of the cap portion is coupled to the second end 25 of the body portion 22, and the second diameter $D_2$ of the cap portion 23 is greater than the first diameter $D_1$ of the body portion 22 so as to form an overhanging lip 29 at the location where the first end 26 of the cap portion 23 is coupled to the second end 25 of the body portion 22. Also, as shown in FIGS. 2 and 3, the dental pin 16 includes a generally rectilinear projection 36 extending from the upper surface 23a, 23b of the cap portion 23 to a predetermined distance H above the upper surface 23a, 23b thereof. The rectilinear projection 36 is configured to matingly engage with a corresponding rectilinear groove 48 in the chuck member 18. The first end 24 of the pin body portion 22 forms the overall distal end of the dental pin 16, whereas the second end 27 of the pin cap portion 23 forms the overall proximal end of the dental pin 16.

Now, with combined reference to FIGS. 2, 3, and 14A, the threads of the dental pin 16 will be described. In FIGS. 2 and 3, it can be seen that the threaded surface 28 extends axially along a length of the pin body portion 22. The threaded surface 28 of the pin body portion 22 comprises a plurality of buttress threads 30 having upper surfaces 32 that are disposed generally perpendicular to the central longitudinal axis LA1. The buttress threads 30 also have angled lower surfaces 34 that are disposed at an acute angle $\theta_2$ relative to the central longitudinal axis LA1 (e.g., refer to FIG. 14A). The upper and lower surfaces 32, 34 form cross sectional angles $\theta_1$ of 45 degrees plus or minus 10 percent (e.g., see FIG. 14A). That is, the respective upper and lower surfaces 32, 34 of the plurality of buttress threads 30 form cross-sectional angles of between approximately 40.5 degrees and approximately 49.5 degrees (or between 40.5 degrees and 49.5 degrees). More particularly, in one embodiment, the respective upper and lower surfaces 32, 34 of the plurality of buttress threads 30 may form cross-sectional angles of approximately 45 degrees.

Figure 14A:
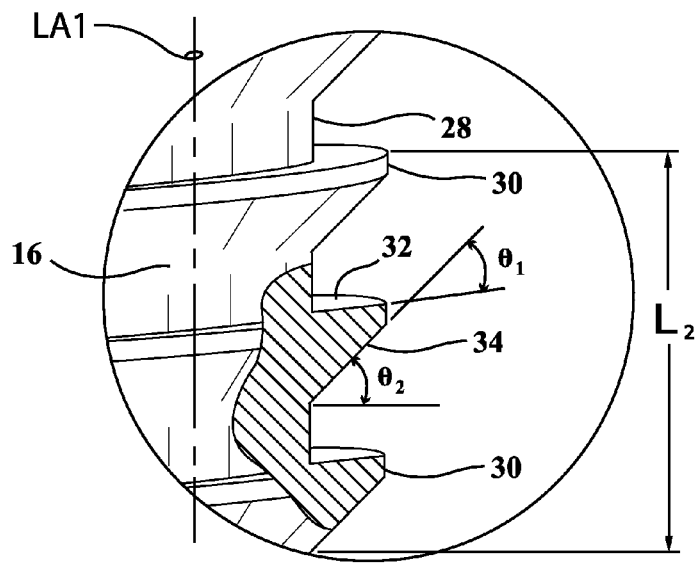
FIG. 14A is an enlarged side elevational view, partly in cross-section, of the dental pin illustrated in FIG. 2 (Detail "B"), wherein the dental pin comprises coarse threads.
Figure 14B:
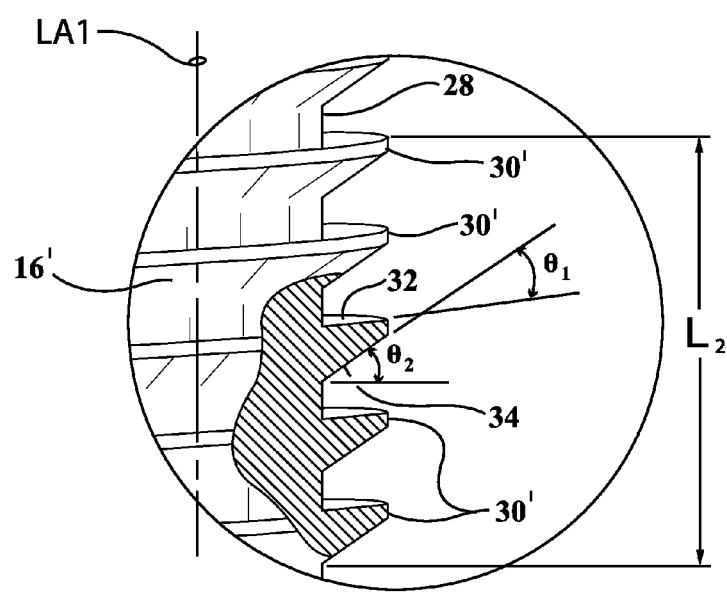
FIG. 14B is an enlarged side elevational view, partly in cross-section, of a dental pin similar to that of FIG. 14A, except the dental pin comprises fine threads, rather than coarse threads.

While dental pins 16 having coarse-type buttress threads 30 are illustrated in FIGS. 2, 3, and 14A, it is to be understood that other dental pins 16' may comprise fine-type buttress threads 30', rather than coarse-type buttress threads 30. For example, a portion of a dental pin 16' comprising fine-type buttress threads 30' is shown in FIG. 14B. As depicted in this figure, when an exemplary dental pin 16' has fine buttress threads 30', there are five threads per an axial distance $L_2$. In contrast, with reference to FIG. 14A, when an exemplary dental pin 16 has coarse buttress threads 30, there are only three threads per the same axial distance $L_2$.

Referring again to FIGS. 2 and 3, as described above, the proximal end of the dental pin 16 (i.e., the second end 27 of the pin cap portion 23) is formed with an upwardly extending generally rectilinear projection 36 for coupling purposes. The opposite, distal end of the dental pin 16 (i.e., the first end 24 of the pin body portion 22) is formed with recessed facets 38 for self-tapping purposes when drilled into the tooth through the exterior surface for reinforcing the tooth. Also, as shown in FIGS. 2 and 3, the distal end of the dental pin 16 (i.e., the first end 24 of the pin body portion 22) comprises a pointed tip 21. The body portion 22 of the dental pin 16 also comprises a non-threaded surface 40 disposed between the pointed tip 21 and the threaded surface 28 so as to facilitate heat dissipation when the dental pin 16 is being driven into a tooth.

In an exemplary embodiment, the dental pin 16 may be fabricated of gold-plated stainless steel so that it does not corrode in the mouth of the patient. Also, in an exemplary embodiment, the dental pin 16 may have an overall length $L_1$ between approximately 4.0 millimeters and approximately 4.9 millimeters, inclusive (or between 4.0 millimeters and 4.9 millimeters, inclusive). More particularly, in one exemplary embodiment, the dental pin 16 may have an overall length $L_1$ of approximately 4.4 millimeters.

Figure 6:
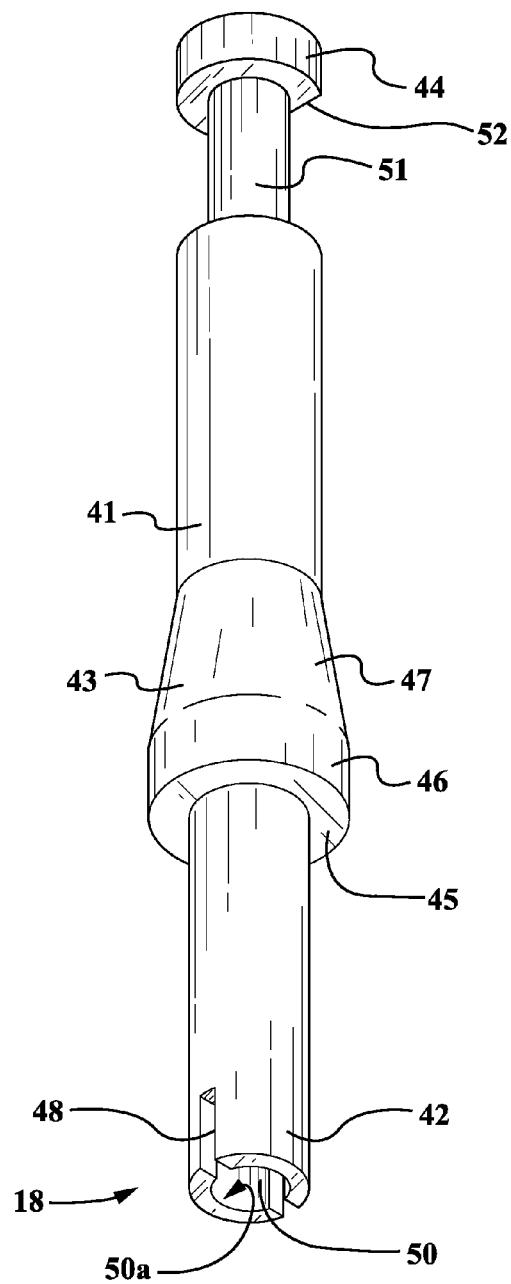
FIG. 6 is a perspective view of a chuck of the dental pin system of FIG. 1.
Figure 9:
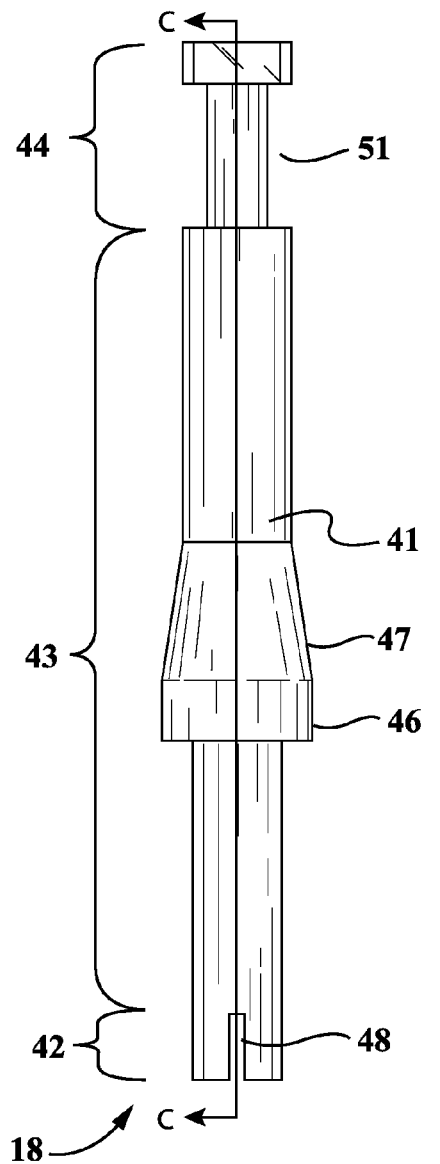
FIG. 9 is a rear elevational view of the chuck of FIG. 6.
Figure 10:
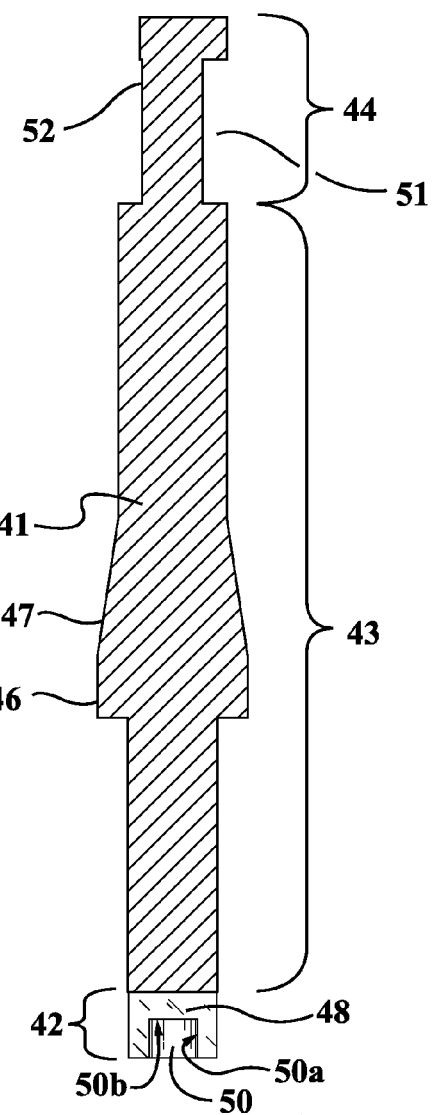
FIG. 10 is another longitudinal sectional view of the chuck of FIG. 6, which is cut along the cutting-plane line C-C in FIG. 9.
Figure 11:
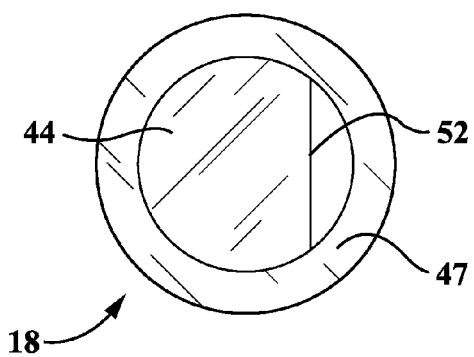
FIG. 11 is a top plan view of the chuck of FIG. 6.
Figure 12:
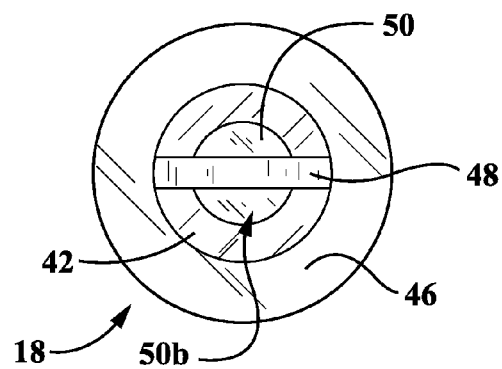
FIG. 12 is a bottom plan view of the chuck of FIG. 6.
Figure 13:
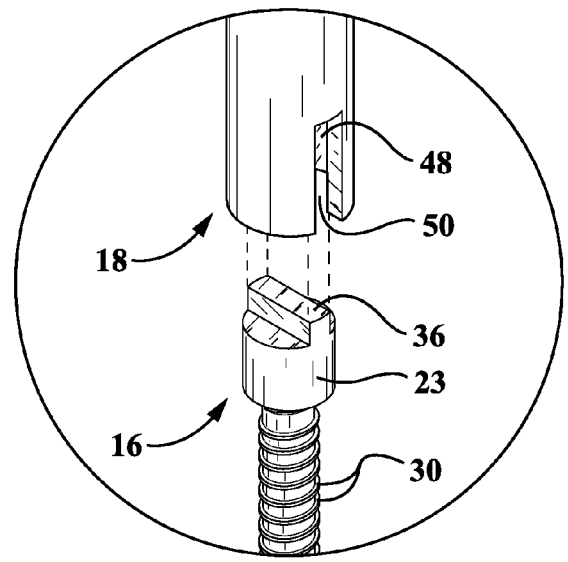
FIG. 13 is an enlarged, partial perspective view of the engagement between the distal end of the chuck and the proximal end of the pin of the dental pin system of FIG. 1 (Detail "A")
Figure 15:
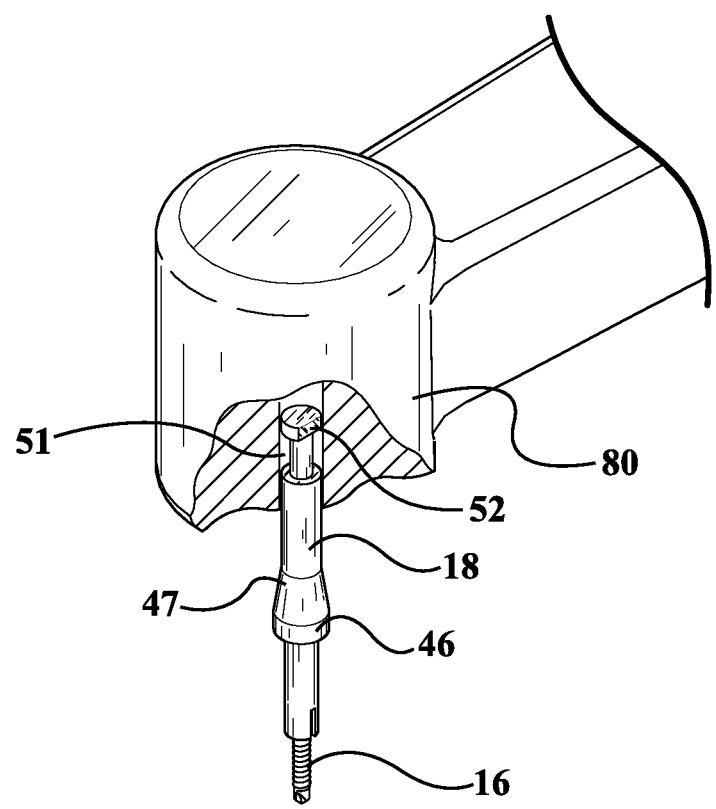
FIG. 15 is a partial, cutaway perspective view generally illustrating the engagement between the dental tool and the chuck of FIG. 1, and the engagement between the dental pin and the chuck of FIG. 1.

Next, referring to FIGS. 6-12, a chuck or chuck member 18 of the exemplary dental pin system 10 will be explained in detail. Initially, as shown in FIGS. 6-8, it can be seen that the chuck member 18 has a generally cylindrical configuration with a central longitudinal axis LA2 disposed axially through the center thereof (e.g., see FIG. 8). The chuck member 18 generally includes a body portion 41 having a first end section 42, a second end section 44 disposed opposite to the first end section 42, and a middle section 43 disposed between the first and second end sections 42, 44. The second end section 44 of the chuck body portion 41 is configured to be removably coupled to a dental tool that drives the chuck member 18, such as the dental tool 80 (e.g., a contra-angle or drill) illustrated in FIGS. 1, 15, and 18. As best shown in FIGS. 6, 8, and 10, the chuck member 18 has a generally cylindrical recess 50 formed in the first end section 42 of its body portion 41. The generally cylindrical recess 50 is bounded by one or more side surfaces (i.e., semi-circular side surfaces 50a) and a circular end surface 50b (e.g., see FIGS. 6, 8, and 10). The generally cylindrical recess 50 is configured to be removably coupled to the cap portion 23 of the dental pin 16. The generally cylindrical recess 50 has a diameter that substantially corresponds to the outer diameter of the pin cap portion 23 and the pin rectilinear projection 36 so that the pin cap portion 23 is received within the generally cylindrical recess 50 of the chuck member 18 with a slight friction fit for preventing the pin 16 from becoming inadvertently dislodged from the chuck member 18 as it is being transferred from the dispenser 20 to the tooth of the patient. With reference to FIGS. 6, 8-10, and 12, it can be seen that the chuck member 18 further includes a generally rectilinear groove 48 formed in the first end section 42 of the body portion 41 and intersecting the generally cylindrical recess 50. As best shown in the bottom view of FIG. 12, the generally rectilinear groove 48 in the first end section 42 of the chuck member 18 bisects the end surface 50b of the generally cylindrical recess 50. The generally rectilinear groove 48 is configured to be removably coupled to the rectilinear projection 36 of the dental pin 16.

Referring again to FIGS. 6-10, it can be seen that the second end section 44 of the chuck body portion 41 comprises a semi-circular groove 51 formed therein. The semi-circular groove 51 is configured to matingly engage with one or more components of the dental tool 80. The second end section 44 of the chuck body portion 41 further comprises a radial flat 52 formed on one side thereof (e.g., see FIGS. 6, 7, 10, and 11). The radial flat 52 of the second end section 44 of the chuck body portion 41 is configured to interlock the chuck member 18 with a rotating component of the dental tool 80.

As additionally shown in FIGS. 6-10, the middle section 43 of the chuck body portion 18 includes an outwardly extending skirt 47 for stabilizing the chuck member 18 as it is being driven by the dental tool 80. As illustrated in these figures, the outwardly extending skirt 47 has a generally frusto-conical shape. An intermediate cylindrical portion 46 is disposed at the base of the frusto-conical skirt 47. The bottom of the intermediate cylindrical portion 46 comprises an overhanging lip 45 that is disposed between the bottom circular edge of the intermediate cylindrical portion 46 and the top circular edge of the cylindrical shaft of reduced diameter that forms the first end section 42 of the chuck member 18.

With reference again to FIGS. 6-10, it can be seen that the chuck member 18 has a distal end (i.e., at the bottom end of the first end section 42), a proximal end (i.e., at the top end of the second end section 44), and a middle body portion (i.e., middle section 43) between the distal and proximal ends. The middle body portion 43 includes a frusto-conical skirt section 47 for stabilization. The distal end of the chuck has the generally rectilinear groove 48 adapted to receive and removably retain the rectilinear projection 36 of the proximal end of the dental pin 16. The distal end of the chuck member also comprises the generally cylindrical recess 50 that is adapted to receive and removably retain the proximal end of the dental pin 16. When the proximal end of the dental pin 16 is fully inserted into the chuck member 18, the top semi-circular surfaces 23a, 23b of the pin cap portion 23 abut the solid circular end surface 50b of the chuck member 18, and the rectilinear projection 36 of the pin 16 bisects the circular end surface 50b of the chuck member 18 and is seated into the portion of the rectilinear recess 48 of the chuck member 18 this is disposed above the cylindrical recess 50 (i.e., the portion of the rectilinear recess 48 that is disposed above the cylindrical recess 50 in FIG. 8). The proximal end of the chuck member 18 comprises a semi-cylindrical head with the radial flat 52 adapted to be removably coupled with the dental tool 80 (e.g., a contra-angle or drill) for drilling purposes.

In an exemplary embodiment, the chuck member 18 may be fabricated of stainless steel so that it is sufficiently durable and does not corrode or rust.

Figure 16:
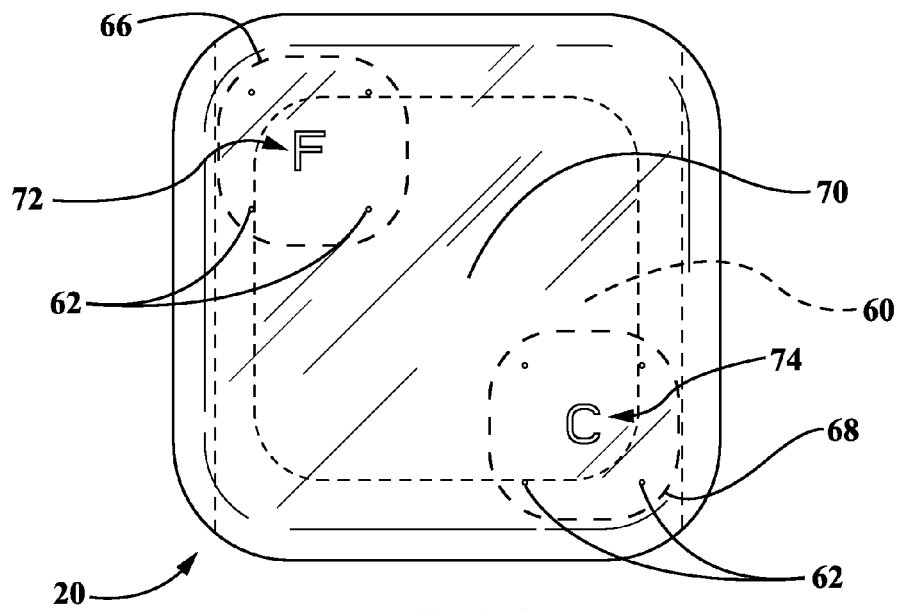
FIG. 16 is a top plan view of a dispenser of the dental pin system of FIG. 1.
Figure 17:
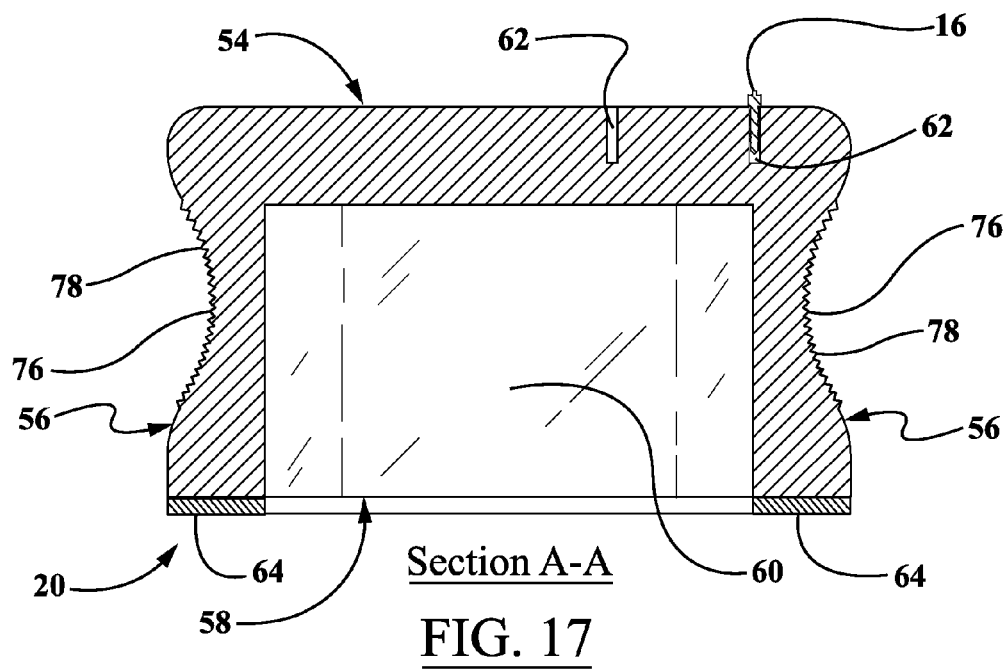
FIG. 17 is a transverse sectional view of the dispenser of FIG. 1, which is cut along the cutting-plane line A-A in FIG. 1.

Now, with reference to FIGS. 1, 16, and 17, a dispenser 20 of the exemplary dental pin system 10 will be described in detail. The dispenser 20 removably supports one or more of the dental pins 16, 16' prior to the dental pins 16, 16' being inserted into a tooth 14'. Initially, referring to FIGS. 1, 16, 17, it can be seen that the dispenser 20 has a generally cubical configuration with an upper surface 54, four side surfaces 56, and a peripheral lower surface 58. As shown in FIGS. 16 and 17, the lower surface 58 of the dispenser 20 is formed with a central cubical recess 60 disposed therein (e.g., to minimize the amount of material forming the dispenser 20). The lower surface 58 of the dispenser 20 is in the form of a peripheral surface that circumscribes the central recess 60. The upper surface 54 of the dispenser 20 has a plurality of holes or cylindrical recesses 62 disposed therein. As shown in FIGS. 1, 16, and 17, the cylindrical recesses 62 in the upper surface 54 of the dispenser 20 are located in relatively close proximity to the side surfaces 56. The cylindrical recesses 62 have a size to removably receive a plurality of pins 16 with the distal ends of the pins 16 facing downwardly and with the proximal ends of the pins 16 exposed for coupling with the chuck member 18. When the dental pins 16 are seated in their respective cylindrical recesses 62 in the dispenser 20, at least a portion of each of the pin body portions 22 is disposed within its respective cylindrical recess 62, while each of the pin cap portions 23 is exposed above the upper surface 54 of the dispenser 20 such that the pin cap portions 23 are capable of being removably coupled to the cylindrical recess 50 of the chuck member 18.

As best shown in the perspective view of FIG. 1 and the top view of FIG. 16, the cylindrical recesses 62 in the upper surface 54 of the dispenser 20 comprise first and second pluralities of recesses 66, 68 (see FIG. 16). As shown in these two figures, each of the pluralities 66, 68 of recesses comprises four (4) recesses 62 arranged in a generally square pattern. The first and second pluralities 66, 68 of cylindrical recesses 62 being separated from one another by a non-perforated portion 70 of the upper surface 54 of the dispenser 20 (e.g., as shown in FIG. 16, the center portion of the upper surface 54 separates the first plurality 66 of four (4) recesses 62 from the second plurality 68 of four (4) recesses 62) so that a user does not easily confuse the two different types of dental pins 16 (i.e., those with coarse and fine threads).

In FIGS. 1 and 16, it can be seen that the first plurality 66 of recesses 62 may include a first indicia 72 disposed proximate thereto, while the second plurality 68 of recesses 62 may comprise a second indicia 74 disposed proximate thereto. The first and second indicia 72, 74 may be imprinted on, inscribed into, or molded in the upper surface 54 of the dispenser 20. The first indicia 72 may include one or more letters or markings that indicate to a user that the first plurality 66 of recesses 62 comprise one or more dental pins 16' with fine threads 30', while the second indicia 74 may include one or more letters or markings that indicate to the user that the second plurality 68 of recesses 62 comprise one or more dental pins 16 with coarse threads 30. In particular, as shown in the illustrative embodiment, the first indicia 72 may be in the form of a capital letter "F" that indicates pins 16' with fine screw threads 30' are disposed adjacent thereto, while the second indicia 74 may be in the form of a capital letter "C" that indicates pins 16 with coarse screw threads 30 are disposed adjacent thereto.

Referring again to the perspective view of FIG. 1 and the transverse sectional view of FIG. 17, it can be seen that two (2) opposed side surfaces 56 of the dispenser are provided with concave indentations 76 disposed along the lengths thereof for enhancing the grip of a user when he or she is grasping the dispenser 20. To further enhance the grip of the user when he or she is grasping the dispenser 20, the outer surfaces of the concave indentations 76 on the opposed side surfaces 56 of the dispenser 20 may additionally comprise a knurled surface 78. Alternatively, rather than a knurled surface, the outer surfaces of the concave indentations 76 on the opposed side surfaces 56 of the dispenser 20 may comprise scoring or spaced-part projections.

In an exemplary embodiment, the dispenser may be molded from a suitable polymeric material, such as a suitable elastomer or plastic. As depicted in the illustrated embodiment, the peripheral lower surface 58 may comprise a skid-resistant layer 64 disposed thereon that is adapted to abate or minimize the movement of the dispenser 20 during use (see FIG. 17). For example, the skid-resistant layer 64 may comprise a thin layer of foam or rubber that increases the coefficient of friction between the bottom of the dispenser 20 and the surface on which it rests (e.g., a top surface of a table or tray).

The illustrative dental pin system 10 described herein is in the form of a kit which aids the dentist in restoring teeth that require a pin-retained core or pin-retained fillings. The dental pin portion 16 of the kit provides the means by which the core is attached to the tooth structure, normally the dentin (e.g., as shown in FIG. 18, dental pins 16 are inserted into cylindrical apertures or recesses 15 in the partial tooth 14'). In FIG. 18, the teeth 14, which are disposed adjacent to the damaged tooth 14', are full healthier teeth. This dental pin kit or system 10 is designed to work specifically in older and more sclerotic dentin but functions equally as well in both healthy and sclerotic dentin. It is more retentive than previous pins due to the employment of a buttress thread 30, 30' and the pointed tip 21 with recessed facets 38. The delivery of the pin 16 is greatly facilitated by having the separate chuck member 18 which acts both as a holder and driver of the pin 16. The dispenser 20 makes the entire process faster, more convenient to use, and more hygienic.

Advantageously, the dental pin system 10 described herein obviates the need for the practitioner to pick up a pin and load it into a dental contra-angle manually. Rather, with the aforedescribed dental pin system 10, the chuck member 18 is placed over the dental pin 16 and rotated to frictionally engage the pin 16 and lift it from the dispenser 20, thus improving the loading and transport of the pin 16. In addition, the ability to autoclave the system 10 and the delivery mode make it more hygienic.

Because the above-described dental pin system 10 utilizes a separate chuck system in which the pins are not self-shearing, and relies on separation of chuck 18 and pin 16, there is increased control of the pin placement and there is less risk of damage to nearby structures during pin placement. In addition, premature separation of chuck 18 and pin 16 is eliminated, thereby allowing the pin 16 to seat completely. Because the pin 16 and chuck 18 are not one-piece, rocking of the assembly 16, 18 to detach the pin 16 from the chuck 18 is unnecessary thus eliminating the risk of loosening or dislodging the pin 16. Finally, using a separate chuck 18 and pins 16 allows for the addition of a cap 23 on the head of the pin 16 that provides increased retention of the core material. The inferior border of the cap 23 provides an undercut that serves to retain the core material mechanically. The physical attributes of the superior portion of the cap 23 help stabilize the entire mechanism during the insertion process.

Advantageously, the illustrative dental pins 16 of the dental pin system 10 described above have the following beneficial attributes:

(1) the pins 16 are the proper universal length so as to provide adequate occlusal clearance;

(2) the pins 16 may be made of stainless steel that allows for unrestricted preparation of the core;

(3) the pins 16 utilize a faceted tip that increases retention by resisting rotation; and (4) the pins 16 utilize a buttress thread form (e.g., with an approximately 45 degree angle) that is designed to handle extremely high axial thrust in one direction, thereby greatly increasing pin retention;

(5) the pins 16 include a cap portion 23 that allows for more torque in driving the pin 16 into the dentin, as well as providing for more retention of the core.

The function of the dental pin 16 described herein is to act as a retentive element after it is driven into tooth structure 14'. The pin 16 serves as an attachment mechanism for the core or filling. The core acts as a foundation for either a pin-retained filling, a crown, or a fixed bridge. The core may be composed of composite resin, amalgam, or glass ionomer cement. As described above, in one or more embodiments, the dental pin 16 is fabricated from 303 gold-plated stainless steel. In an exemplary embodiment, the dental pin 16 may be approximately 4.4 millimeters (mm) in length, approximately 0.0270 inches at its major diameter and approximately 0.0230 inches at its minor diameter. In general, the component parts of the pin 16 are the head, shaft, and tip. In an exemplary embodiment, the head length is approximately 0.05 inches, the shaft length is approximately 0.13 inches, and the tip length is approximately 0.03 inches.

In one or more embodiments, the dental pin 16 may comprise a buttress thread 30 that has a lead angle of approximately 45 degrees. The thread can be ground in such a manner that it acts as either a coarse or fine thread, using the number of threads per inch as a criterion. The tip 21 of the dental pin 16 is sharply pointed so that the pin 16 can be either self-tapping or can be inserted into a pre-drilled hole (e.g., the generally cylindrical hole 15 in the tooth 14' of FIG. 18). The tip 21 is designed so that when it is driven into its channel, it engages the bottom of the channel with the edges of the tip for greater retention.

As described above, the head of the pin 16 has a cap portion 23 with an extended projection 36 that fits into the chuck member 18 with very close tolerance. The shaft of the dental pin 16 is cylindrical with a helical pattern of threads 30, extending from approximately the bottom of the head to a distance above the tip 21 (see e.g., FIGS. 2 and 3). The non-threaded surface 40 is disposed between the tip 21 and the bottommost thread 30.

The function of the chuck member 18 is to engage and drive the dental pin 16 into the tooth structure (e.g., tooth 14' in FIG. 18). The dental tool 80 (e.g., contra-angle or drill) retains and drives the chuck member 18. As the dental tool 80 (e.g., contra-angle or drill) rotates, it picks up the pin 16 from the dispenser 20 and carries the pin 16 from the dispenser 20 to the oral cavity to be driven into the tooth structure (e.g., tooth 14' in FIG. 18). The chuck member 18 aids in the process of placing the pin 16 in the pilot hole (e.g., hole 15 in FIG. 18) and, while rotating, drives the pin 16 into the dentin of the tooth. As described above, in an exemplary embodiment, the chuck member 18 may be formed from 300 series stainless steel. The top of the chuck member 18 is designed to fit into either a latch-type or push type dental tool 80 (e.g., a latch-type or push type contra-angle). As explained in detail above, the mid-portion of the chuck member 18 has a skirt 47 that aids in the stability of the chuck 18 while rotating.

As shown in the illustrated embodiment of FIGS. 1, 16, and 17, the dispenser 20 is a box-like square with apertures or holes 62 in the top surface 54 that hold pins 16 to be driven into tooth structure (e.g., tooth 14' in FIG. 18). As explained above, the base of the dispenser 20 may include a strip that acts as a non-skid element (e.g., skid-resistant layer 64) to brace the dispenser 20 while the practitioner engages the pin 16 with a chuck 18. The sides 56 of the dispenser 20 may be indented and scored so as to increase the grip of the user on the dispenser 20 while it is in use.

In one or more embodiments, the dispenser 20 containing both fine and coarse pins 16, 16' is placed on the dental bracket table. The dental tool 80 (e.g., reduction gear contra-angle) is inserted into a slow-speed dental handpiece. The chuck 18 is inserted into the contra-angle and placed over the top of the pin 16 and rotated. The chuck 18 then picks up the pin 16 from the dispenser 20 and carries it to the oral cavity. In the case of the pre-drilled hole (e.g., hole 15 in FIG. 18), the tip of the pin 16 then engages the top of the pilot hole, and the contra-angle and chuck 18 drive the pin 16 until it reaches the bottom of the channel. In the case of the self-tapping pin 16, the pin 16 is driven to the desired depth into the dentin without the need for a pre-drilled hole.

Advantageously, the dental pins 16 of the dental pin system 10 described herein are not in the form of self-shearing type pins, which are susceptible to premature separation from their driving means and/or an inability to be separated from the driving means when needed or desired. As such, the dental pins 16 described herein do not comprise multiple shearing sections with areas of weakness (e.g., grooves or reduced diameter sections) disposed between the shearing sections. In addition, the aforedescribed dental pins 16 do not comprise topmost projections that have a transverse width greater than that of any other portion of the pin 16. Rather, as described above, the rectilinear projections 36, which extend upwardly from the cap portions 23 of the dental pins 16, have a transverse width that is generally equal to the diameter of the cap portion 23 (e.g., see FIGS. 2 and 3).

It is readily apparent that the dental pin system 10 offers numerous advantages. First, the dental pin system 10 utilizes a separate, reusable chuck 18 for effectively driving the dental pin 16 into the tooth. Secondly, the dental pin system 10 advantageously includes a dental pin 16 that, once it has separated from its chuck 18, has a cap or cap portion 23 that provides more torque to drive it and provides increased retention of the core material on the tooth being repaired. Finally, the dental pin system 10 includes an effective and hygienic means by which to dispense and insert the pins into one or more teeth.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A dental pin for insertion into a tooth, said dental pin comprising:

a body portion having a first end, a second end disposed opposite to said first end, a first diameter, and a central longitudinal axis, said body portion further including a peripheral sidewall comprising a threaded surface, said first end of said body portion comprising a pointed tip with a plurality of recessed facets, each of said plurality of recessed facets being disposed diagonally opposite one another and symmetrically arranged with respect to said central longitudinal axis, said peripheral sidewall of said body portion further comprising a cylindrical non-threaded surface between said pointed tip and said threaded surface so as to facilitate heat dissipation, said cylindrical non-threaded surface circumscribing said peripheral sidewall, a first lower portion of said cylindrical non-threaded surface being intersected by a portion of each of said plurality of recessed facets, a second upper portion of said cylindrical non-threaded surface being disposed between upper ends of said plurality of recessed facets and a lower end of said threaded surface;
a cap portion having a first end, a second end disposed opposite to said first end, and a second diameter, said first end of said cap portion coupled to said second end of said body portion, said second diameter of said cap portion being greater than said first diameter of said body portion so as to form an overhanging lip at the location where said first end of said cap portion is coupled to said second end of said body portion, said cap portion further including a peripheral sidewall and an upper surface, said upper surface of said cap portion disposed at a top of said peripheral sidewall of said cap portion, said cap portion configured to removably engage with a recess in a chuck member, said cap portion further configured to remain on said body portion of said dental pin after said dental pin has been inserted into a damaged tooth so as to increase a retention of core material on said damaged tooth; and
a projection extending from said upper surface of said cap portion, said projection having a first side surface, a second side surface disposed opposite to said first side surface, a first end surface, and a second end surface disposed opposite to said first end surface, said first and second end surfaces aligned with said peripheral sidewall of said cap portion, said projection dividing said upper surface of said cap portion into a first upper flat surface portion and a second upper flat surface portion, said first and second upper flat surface portions being disposed on respective opposite sides of said projection, said first and second upper flat surface portions adjoining respective said first and second side surfaces of said projection at respective right angle corners, said projection configured to removably engage with a corresponding groove in said chuck member.

2. The dental pin according to claim 1, wherein said threaded surface of said body portion comprises a plurality of buttress threads, each of said plurality of buttress threads having an upper surface and a lower surface.

3. The dental pin according to claim 2, wherein said upper and lower surfaces of said plurality of buttress threads form cross-sectional angles of between approximately 40.5 degrees and approximately 49.5 degrees.

4. The dental pin according to claim 2, wherein said upper surfaces of said plurality of buttress threads are disposed generally perpendicular to said central longitudinal axis of said body portion, and said lower surfaces of said plurality of buttress threads are disposed at an acute angle relative to said central longitudinal axis.

5. The dental pin according to claim 1, wherein said threaded surface of said body portion comprises either a plurality of coarse threads or a plurality of fine threads.

6. The dental pin according to claim 1, wherein each of said body portion and said cap portion is generally cylindrical in shape.

7. The dental pin according to claim 1, wherein said projection has a generally rectilinear shape, said projection extending a predetermined distance above said first and second upper flat surface portions of said cap portion, said predetermined distance being less than said second diameter of said cap portion.

8. A chuck member for inserting a dental pin into a tooth, said chuck member comprising:
a body portion having a first end section, a second end section disposed opposite to said first end section, and a middle section disposed between said first and second end sections, said middle section including a first longitudinal portion having a first cross-sectional area and a second longitudinal portion having a second cross-sectional area, said first cross-sectional area being greater than said second cross-sectional area, said second end section comprising an axially-extending portion with a third cross-sectional area that is less than said first and second cross-sectional areas, said axially-extending portion with said third cross-sectional area being bounded by an annular ledge on a lower end and a C-shaped ledge on an upper end, said C-shaped ledge on said upper end being disposed in a cantilevered manner above said annular ledge on said lower end, said second end section of said body portion configured to be removably coupled to a dental tool that drives said chuck member, wherein said middle section of said body portion includes an outwardly extending skirt for stabilizing said chuck member as it is being driven by said dental tool, at least a portion of said outwardly extending skirt having a generally frusto-conical shape and an increasing diameter in an axial direction towards said first end section of said body portion, and wherein said first cross-sectional area of said first longitudinal portion of said middle section is consistent from said annular ledge to said outwardly extending skirt;
a recess formed in said first end section of said body portion, said recess being bounded by one or more side surfaces and an end surface, said recess configured to be removably coupled to a cap portion of a dental pin; and
a groove formed in said first end section of said body portion and intersecting said recess, said groove bisecting said end surface of said recess, said groove extending deeper into said first end section of said body portion than said recess so as to create a step at said end surface of said recess, said groove extending completely through a cross section of said first end section of said body portion along an entire length of said groove, said groove configured to be removably coupled to a projection of said dental pin.

9. The chuck member according to claim 8, wherein said axially-extending portion with said third cross-sectional area is formed by a semi-circular groove in said second end section of said body portion, said semi-circular groove configured to matingly engage with one or more components of said dental tool.

10. The chuck member according to claim 8, wherein said second end section of said body portion further comprises a radial flat formed on one side thereof, said radial flat forming a bounding edge of said C-shaped ledge, said radial flat configured to interlock said chuck member with a rotating component of said dental tool.

11. The chuck member according to claim 8, wherein said recess formed in said first end section of said body portion is generally cylindrical in shape.

12. The chuck member according to claim 8, wherein said groove formed in said first end section of said body portion has a generally rectilinear shape.

13. A dental pin system comprising, in combination:
a chuck member for inserting a dental pin into a tooth, said chuck member including:
a chuck body portion having a first end section, a second end section disposed opposite to said first end section, and a middle section disposed between said first and second end sections, said middle section including a first longitudinal portion having a first cross-sectional area and a second longitudinal portion having a second cross-sectional area, said first cross-sectional area being greater than said second cross-sectional area, said second end section comprising an axially-extending portion with a third cross-sectional area that is less than said first and second cross-sectional areas, said axially-extending portion with said third cross-sectional area being bounded by an annular ledge on a lower end and a C-shaped ledge on an upper end, said C-shaped ledge on said upper end being disposed in a cantilevered manner above said annular ledge on said lower end, said second end section of said chuck body portion configured to be removably coupled to a dental tool that drives said chuck member, wherein said middle section of said chuck body portion includes an outwardly extending skirt for stabilizing said chuck member as it is being driven by said dental tool, at least a portion of said outwardly extending skirt having a generally frusto-conical shape and an increasing diameter in an axial direction towards said first end section of said chuck body portion, and wherein said first cross-sectional area of said first longitudinal portion of said middle section is consistent from said annular ledge to said outwardly extending skirt;

a recess formed in said first end section of said chuck body portion, said recess being bounded by one or more side surfaces and an end surface; and a groove formed in said first end section of said chuck body portion and intersecting said recess, said groove bisecting said end surface of said recess, said groove extending deeper into said first end section of said chuck body portion than said recess so as to create a step at said end surface of said recess, said groove extending completely through a cross section of said first end section of said chuck body portion along an entire length of said groove; and a dental pin including:
  a pin body portion having a first end, a second end disposed opposite to said first end, a first diameter, and a central longitudinal axis, said pin body portion further including a peripheral sidewall comprising a threaded surface, said first end of said pin body portion comprising a pointed tip with a plurality of recessed facets, each of said plurality of recessed facets being disposed diagonally opposite one another with respect to said central longitudinal axis, said peripheral sidewall of said pin body portion further comprising a cylindrical non-threaded surface between said pointed tip and said threaded surface so as to facilitate heat dissipation, said cylindrical non-threaded surface being intersected by a portion of each of said plurality of recessed facets;
  a pin cap portion having a first end, a second end disposed opposite to said first end, and a second diameter, said first end of said pin cap portion coupled to said second end of said pin body portion, said second diameter of said pin cap portion being greater than said first diameter of said pin body portion so as to form an overhanging lip at the location where said first end of said pin cap portion is coupled to said second end of said pin body portion, said pin cap portion further including a peripheral sidewall and an upper surface, said upper surface of said pin cap portion disposed at a top of said peripheral sidewall of said pin cap portion, said pin cap portion configured to be removably coupled to said recess of said chuck member, said pin cap portion further configured to remain on said pin body portion of said dental pin after said dental pin has been inserted into a damaged tooth so as to increase a retention of core material on said damaged tooth; and
  a projection extending from said upper surface of said pin cap portion, said projection having a first side surface, a second side surface disposed opposite to said first side surface, a first end surface, and a second end surface disposed opposite to said first end surface, said first and second end surfaces aligned with said peripheral sidewall of said cap portion, said projection dividing said upper surface of said pin cap portion into a first upper flat surface portion and a second upper flat surface portion, said first and second upper flat surface portions being disposed on respective opposite sides of said projection, said first and second upper flat surface portions adjoining respective said first and second side surfaces of said projection at respective right angle corners, said projection configured to be removably coupled to said groove of said chuck member.

14. The dental pin system according to claim 13, further comprising a dispenser for removably supporting one or more of said dental pins prior to said dental pins being inserted into a tooth, said dispenser having an upper surface, one or more side surfaces, and a lower surface, said upper surface of said dispenser including one or more recesses disposed therein for removably receiving said one or more dental pins, said one or more recesses in said upper surface of said dispenser being generally cylindrical in shape, wherein at least one of said one or more side surfaces comprises a concave indentation to enhance a grip of a user, and wherein at least a portion of said pin body portion of each of said one or more dental pins is disposed within its respective said recess, and said pin cap portion of each of said one or more dental pins is exposed above said upper surface of said dispenser such that said pin cap portion is capable of being removably coupled to said recess of said chuck member.

15. The dental pin system according to claim 14, wherein said lower surface of said dispenser has a central recess formed therein, and wherein said lower surface of said dispenser is in the form of a peripheral surface that circumscribes said central recess, said lower surface of said dispenser comprising a skid-resistant layer disposed thereon that is adapted to minimize the movement of said dispenser during use.

16. The dental pin system according to claim 14, wherein said one or more recesses in said upper surface of said dispenser comprise first and second pluralities of recesses, said first and second pluralities of recesses being separated from one another by a non-perforated portion of said upper surface of said dispenser, said non-perforated portion being centrally located in said upper surface of said dispenser between said first and second pluralities of recesses, and wherein said first plurality of recesses comprises a first indicia disposed proximate thereto, and said second plurality of recesses comprises a second indicia disposed proximate thereto.

17. The dental pin system according to claim 16, wherein said first indicia comprises one or more letters or markings that indicate to a user that said first plurality of recesses comprise said one or more dental pins with fine threads, and wherein said second indicia comprises one or more letters or markings that indicate to said user that said second plurality of recesses comprise said one or more dental pins with coarse threads.

18. The dental pin system according to claim 17, wherein said first and second pluralities of recesses are diagonally arranged with respect to one another on opposite sides of said non-perforated portion of said upper surface of said dispenser.

19. The dental pin system according to claim 18, wherein said first plurality of recesses comprises recesses arranged in a first symmetrical pattern and said second plurality of recesses comprises recesses arranged in a second symmetrical pattern; and wherein said first indicia is centrally disposed within said first symmetrical pattern of said first plurality of recesses and said second indicia is centrally disposed within said second symmetrical pattern of said second plurality of recesses.

\* \* \* \* \*